(12) United States Patent
Strobel

(10) Patent No.: US 9,114,167 B2
(45) Date of Patent: Aug. 25, 2015

(54) METHOD FOR SOLUBILISING, DISPERSING AND STABILISING OF SUBSTANCES, PRODUCTS MANUFACTURED ACCORDING TO THE METHOD AS WELL AS THE USE THEREOF

(71) Applicant: Biorem AG, Baar (CH)

(72) Inventor: Hanspeter Strobel, Davos-Platz (CH)

(73) Assignee: Biorem AG, Baar (CH)

( * ) Notice: Subject to any disclaimer, the term of this patent is extended or adjusted under 35 U.S.C. 154(b) by 3 days.

(21) Appl. No.: 14/184,145

(22) Filed: Feb. 19, 2014

(65) Prior Publication Data

US 2014/0193513 A1 Jul. 10, 2014

Related U.S. Application Data

(62) Division of application No. 12/281,834, filed as application No. PCT/CH2007/000131 on Mar. 9, 2007, now Pat. No. 8,703,195.

(30) Foreign Application Priority Data

Mar. 10, 2006 (CH) .......................... 377/06

(51) Int. Cl.

| A61K 47/32 | (2006.01) |
|---|---|
| A61K 47/10 | (2006.01) |
| A61K 38/13 | (2006.01) |
| A61K 31/7048 | (2006.01) |
| A61K 31/122 | (2006.01) |
| A61K 8/02 | (2006.01) |
| A61K 47/22 | (2006.01) |
| A61K 47/34 | (2006.01) |
| A61K 35/644 | (2015.01) |
| A61K 38/28 | (2006.01) |
| A61K 9/14 | (2006.01) |
| A61K 8/98 | (2006.01) |
| A61K 35/04 | (2006.01) |
| A01N 25/02 | (2006.01) |
| A01N 25/04 | (2006.01) |
| A01N 43/90 | (2006.01) |
| A61K 8/67 | (2006.01) |
| A61K 8/90 | (2006.01) |
| A61Q 5/02 | (2006.01) |

(52) U.S. Cl.
CPC .............. *A61K 47/32* (2013.01); *A01N 25/02* (2013.01); *A01N 25/04* (2013.01); *A01N 43/90* (2013.01); *A61K 8/0291* (2013.01); *A61K 8/678* (2013.01); *A61K 8/90* (2013.01); *A61K 8/988* (2013.01); *A61K 9/146* (2013.01); *A61K 31/122* (2013.01); *A61K 31/7048* (2013.01); *A61K 35/04* (2013.01); *A61K 35/644* (2013.01); *A61K 38/13* (2013.01); *A61K 38/28* (2013.01); *A61K 47/10* (2013.01); *A61K 47/22* (2013.01); *A61K 47/34* (2013.01); *A61Q 5/02* (2013.01)

(58) Field of Classification Search
CPC ..... A61K 47/32; A61K 35/644; A61K 9/146; A61K 8/988; A61K 8/678; A61K 38/28; A61K 8/90; A61K 35/04; A61K 41/10; A61K 47/34; A61K 47/30; A61K 38/13; A61K 31/05; A61K 31/095; A61K 47/10; A61K 47/22; A61K 8/0291; A61K 31/122; A61K 31/7048; A01N 25/02; A01N 43/90; A01N 25/04; A61Q 5/02; A01K 35/08; A01K 36/28

See application file for complete search history.

(56) References Cited

FOREIGN PATENT DOCUMENTS

WO   WO 2006024138 A1 * 3/2006

* cited by examiner

*Primary Examiner* — John Pak
*Assistant Examiner* — Andriae M Holt
(74) *Attorney, Agent, or Firm* — CUSPA Technology Law Associates, P.A.; Yi Li

(57) ABSTRACT

Disclosed is a method in which poloxamer, a resin, and/or a tocopherol is/are fused, and the material that is to be treated is intimately dispersed with said melt. After being introduced into the melt, the material that is to be treated is coated with water to prevent hardening, and the spontaneously forming gel is homogenized. The obtained product is composed of a transparent gel that is based on at least one poloxamer, a resin or a tocopherol, and an active substance which is solubilized, dispersed, and stabilized therein and whose consistency ranges from solid, semisolid, i.e. aspic-like, to liquid. The micelles of said solubilized matter remain stable even when the same is diluted well below the CMC of poloxamer.

8 Claims, No Drawings

METHOD FOR SOLUBILISING, DISPERSING AND STABILISING OF SUBSTANCES, PRODUCTS MANUFACTURED ACCORDING TO THE METHOD AS WELL AS THE USE THEREOF

This application is a divisional of patent application Ser. No. 12/281,834, filed Nov. 18, 2008, which is a national phase of PCT application No. PCT/CH2007/000131, filed Mar. 9, 2007, which claims priority of Swiss patent application No. 377/06, filed Mar. 10, 2006. The parent applications are hereby incorporated by reference.

The present invention relates to a basic method for solubilising, dispersing, stabilising and, if needed, sequestering various substances. These substances are concerned, for instance, not only with lipophiles and resin-like active agents in hydrophilic milieu and with hydrophilic substances in lipophilic milieu, but also with hydrophilic substances to be sequestered in aqueous systems, such as the ones with bitter taste or smell of fish. Sequestering implies suppressing the smell and taste of substances. And finally, there are also solid particles such as pollen and dandruff in aqueous milieu. Along with the solubilising and dispersing of such substances, even when these are active agents, a stabilising of the same in the hydrophilic milieu is also achieved. The invention also relates to all kinds of semi-finished products, concentrates and ready to use products as goods, produced according to this method. The invention especially enables one to provide the active agents, which have proved to be advantageous for the growth of plants, in a form that is easy to apply. For this, these can be crushed dust-free, solubilised, dispersed and, if needed, stabilised, and then applied, so that they are available to the plants for absorption and are also actually absorbed by them. This solubilising method tremendously increases the efficiency of the application of plant active ingredients, and moreover the dust-free execution results in a substantial cost saving, because the production environment now no longer need to be protected against the high toxicity of the vapours of the active agents (herbicides, fungicides, acaricides, pesticides). The solubilising and dispersing of such active agents for plants also achieves a stabilisation of these active agents in the hydrophilic milieu. The stabilisation not only means the stability of the solubilisate, but also its stability on the way to the roots through the earth. The invention, therefore, also covers the formulations of the active agents developed as products according to the method for the plants. Finally, the invention also includes the use of such solubilised products for various commercial purposes, as far as these are not concerned with the therapeutic treatment of the human or the animal body.

One generally looks for auxiliary substances, which trigger, permit, support or simplify the solubilising or the dispersing. It is ideal, when such auxiliary substances are already contained in the lists of drug or fodder, because they are then by no means dubious and there will be no objections or reservations from the health authorities, consumer organisations or other communities of interests that to be worried about. But not only the pure solubilising and dispersing of a substance, namely an active agent, is a subject, because it is often required to stabilise a solubilised active agent, so that it can unfold its effect completely and for a long time and its resorption is improved.

There are some active agents, whose effectiveness is known among experts, however, whose application causes problems, because their solubilisation and as such also their stabilisation causes problems. The coenzyme Q10 can be mentioned as an example. Studies from USA have shown that this active agent could play an important role in combating Parkinson's and Alzheimer's diseases, it also shows positive effects in cancer, AIDS and other infectious diseases. It has already been discovered in the sports medicine that the coenzyme Q10 speeds up the regeneration after injuries. However, coenzyme Q10 is a fat-soluble powder and hence not water-soluble. Active agents that are not water-soluble often possess a poor bioavailability, i.e. they can produce their effect in the organism only less efficiently and less target-oriented. In case of the very expensive active agents, it is very irritating that a major part of the quantity administered cannot be used by the organism, but instead is washed out or separated. And hence, an expensive active agent such as coenzyme Q10 has a bioavailability of merely 10% in practice.

After the publishing of the results of study, according to which the coenzyme Q10, as mentioned, is important for fighting Parkinson's, Alzheimer's, cancer and AIDS, its market price doubled shortly and currently it costs around CHF 2,000 per kg. It is clear that enhancing the bioavailability would mean not only a big technological but also a big economical improvement. If the bioavailability could be doubled, then with the same amount of the available active agents, double the number of humans could be treated.

The possibility of solubilising a fat-soluble active agent of this or similar quality and stabilising it at the same time would open up new, unimagined prospects. Thus, active agents treated in this way could not only be administered orally in the form of capsules, but could also be mixed with a drink, for instance, with a drink for the sportspersons. In view of the fact that the active agents soluble in fat would be soluble in the drink and would also remain stable, would open up completely new business areas for the entire Lifestyle segment. Furthermore, the active agent suspended in the aqueous milieu would not remain sticking to the inner wall of the PET bottle to over 80%, but instead would leave the bottle completely with the fluid carrier and thus enter the body of the person drinking it.

Another important active agent, whose application creates complications, is Insulin. Insulin is a helical peptide with a lot of amino acids, and shows an especially sensitive spatial structure. In order to achieve a suitable bioavailability, it must be injected. This is not very pleasant for the affected persons and is a very cumbersome procedure each time. It would be highly desirable and would also be a great breakthrough, if one could make Insulin available orally. In the West, one-fifth of the total population is suffering from a form of more or less high diabetes, and the percentage of obese people is constantly increasing, thus the number of people having type II diabetes is also on the rise. The importance of insulin would thus rise because of this only and a better form of administration would be much in demand. Insulin is a hormone and, as per the definition, is a substance that controls the important functions of our body in small quantities. Strong and effective control substances must be low-dosed upon their use. Often the auxiliary substances of the solution that can be used are also low-dosed. In the oral route, the applied solubilisate undergoes a further dilution (through saliva, gastric and digestive juices), so that the Critical micelle concentration (cmc) of the tenside used in the solubilisate falls down considerably as expected. In this way, the solubilisate breaks down, after which the insulin is no longer protected against enzymes and pH variations, and thus gets inactivated. An oral administration of insulin, therefore, fails because of this reason.

From the WO 01/19329 A (THE PROCTER & GAMBLE COMPANY) 22 Mar. 2001, a solubilising process has been introduced as the closest to the prior art, in which one produces a molten mass with poloxamer and propylene glycol, in which an alcohol premix of an active agent poorly soluble in water is added and then the whole is finally homogenised with water. In case of such a molten mass the micelles behave according to the text book: They separate out below the critical micelle concentration cmc and the lipophilic active agents precipitate out. Additionally, active agents solubilised in this way are not mixed with each other in any ratio, without the combinations of the individual solubilisates becoming cloudy or getting changed physically or chemically in some other way. Never before has a solubilisation system been mentioned in the technical literature, which makes micelles of various active agents and these micelles also remain stable much below the cmc, so that no precipitation, creaming or opalescence takes place in case of increasing dilution.

Along with medically active agents, there is also a series of non-medical substances, which could not be solubilised or dispersed till now. These active agents are, for instance, lipophiles or resin-like active agents in hydrophilic milieu as also hydrophilic substances in lipophilic or hydrophilic milieu, and finally also solid particles in aqueous milieu, such as a suspension. In experiments, for instance, particles of plant active ingredients were mixed in a higher percentage solubilisate and this was then wet grounded. The final swelled suspension was milled further in hammer or emulsion mill, till the particle size of the powder in the suspension was reduced to about 2 to 5 micrometer. If then such a solution was applied, i.e. put in the soil near the root network for absorption by the plant, and water was poured after that, the root network of the plant surprisingly absorbed only the water and the emulsifiers with its roots, but not the plant active ingredient itself, as expected!

It is ideal, when the plant active ingredients to be provided are already approved and no objections or reservations are to be expected from the authorities, consumer organisations or other communities of interests. However, just the solubilising and dispersing a plant active ingredient is not only of importance, but it is also important that it is made available to the plant actually and efficiently, so that it can actually be absorbed by its root network and can maintain its effect in the plant, till it decays.

There are some plant active ingredients, whose effectiveness is known among experts, however, whose application causes problems, because their solubilisation as well their absorption by the plant is a problem. In case of especially expensive or concentrated plant active ingredients, it is very irritating that a large part of the quantity administered cannot be used at all by the plant, but instead remains lying in the ground and contaminates it. The possibility of solubilising a fat-soluble active ingredient for plants and also stabilising it at the same time, would open up unimagined prospects. The active ingredients for plants treated in this way could be absorbed intact by the plants.

The object of the present invention, therefore, is to specify a basic method, with the help of which such substances can be solubilised, dispersed and stabilised. The method should be reliable, simple and economically feasible and should be applicable for various substances.

A second object of the invention is to develop and specify a number of substances for making usable products using this method.

A third object of the invention is to specify the use of some of the solubilised goods, produced according to this process, for specific purposes.

The first object is fulfilled by a method for solubilising, dispersing and stabilising the substances, which is characterised in that on one hand a poloxamer (polyoxyethylene-polyoxypropylene block copolymer), and on the other a resin and/or a tocopherol are melted together to make a combined molten mass and the substance to be treated is dispersed or dissolved inside this molten mass.

The second object is fulfilled by a product, consisting of a molten mass of a transparent gel on the basis of at least a poloxamer in combination with a natural or a synthetically made resin and/or a tocopherol, as well as an active agent solubilised and stabilised in it, with a consistency between solid and semi-solid, i.e. aspic-type, up to a liquid.

The third object is fulfilled by various uses of products in accordance with the composition mentioned above, which contain specific substances in the solubilised form, for specific commercial purposes as per the usage requirements.

It has proved to be especially important that the auxiliary substances, i.e. here the poloxamer, the resin or the tocopherol and the active agent to be treated combine on a molecular basis and then, and only then, form micelles after the addition of water to prevent a hardening, which remain stable even in a dilution 1000-times less than the critical micelle concentration cmc as loaded micelles. Tocopherol is a defined substance, which occurs in four different stereo-isomers, and depending upon that has an 'IN VIVO' Vitamin E effect or doesn't have. In order to ensure this highly important stability of the micelles even at low concentrations, it is essential that the molten mass is produced from a poloxamer in combination with a natural or a synthetically prepared resin and/or a tocopherol and the active agent to be solubilised is dispersed within that. This molten mass is thereafter covered with a layer of water at the same temperature, which forms a gel, and then it is homogenised. The highly significant advantage of this solubilisation method is the stability of the micelles achieved with this method even to the power of ten below the cmc! This result can be achieved only when a poloxamer is melted and the active agent is used and a natural or synthetically prepared resin and/or tocopherol are dispersed within this molten mass.

If poloxamer is not contaminated with the solvents, it remains liquid at around 57° C. to 58° C. One then finds that in a poloxamer-molten mass, a lot of lipophiles as well as even hydrophilic substance dissolve very well. The addition of a natural or a artificially prepared resin, or a tocopherol in addition to or in place of the resin, and this type of solubilisation, in which one mixes these auxiliary substances in a molten mass on molecular or quasi-molecular basis with the substances to be solubilised, prove as the key for improving the loading factor of the micelles of the active agent thus produced and as the key for achieving a stability of the micelles thus produced even well below their cmc. In this way, one can envelope not only more active agent with the auxiliary substances to form micelles, but also the micelles formed remain absolutely stable even much below the critical micelle concentration. Moreover, only the solubilised active agents, which were produced with resin and/or tocopherol according to this melting method, can be mixed with one another in any ratio, without that the combinations of the individual solubilisates become cloudy or change physico-chemically in some other way.

A critical point in the process is the temperature of the poloxamer-molten mass. It is known that the peptides react vigorously at high temperatures. In the temperature range of 40° C. to 60° C., a lot of proteins get denatured. The colouring of the egg-white while frying an egg in white at 56° C. is the proof of such a structural change of proteins, which anybody could observe. A fever of above 40° C. is unsafe for the patient because of the protein change that sets in. The temperature of the molten mass of poloxamer can be reduced by the addition of suitable solvents. Non-poisonous solvents like glycerin, polypropylene glycol, polyethylene glycol 400, etc. are suitable for this purpose. By adding these solvents in suitable quantities, the melting temperature of Poloxamer can be reduced to such an extent that even the active agents known as thermo-labile, such as insulin or a sensitive plant active ingredient, can also be solubilised and stabilised.

Another process step, optional for certain applications and an important step in this case is that the poloxamer molten mass with the active agent dissolved in it is then immediately covered with an adequately thick layer of water at about the same temperature. This helps in the formation of a transparent gel below the water layer. Without such a covering of water at the same warm temperature, the molten mass would harden like plastic and cannot be applied directly in this form. In order to prevent a hardening, the molten mass should, therefore, be poured over or covered with water at the same temperature while still in the liquid state. The gelation also takes place with cold water, but then mainly a dispersion of the active agent takes place. After water at the same temperature has been added and this water has formed a covering of the molten mass—the water naturally floats above the molten mass—the gelation takes place spontaneously and the gel quickly grows upward in the mass against the water surface, when the molten mass absorbs water. This gelation, observable from outside, is supported by bringing the molten mass and the water in contact, by means of a slight stirring. The gel has a micelle structure with a droplet diameter of less than 80 nm, so that it does not refract light and the gel is absolutely transparent, one can even read a newspaper through this gel, although about 5-10% of this is fat-soluble active agent, approx. 10-20% is a poloxamer and 1-15% is a natural or an artificially prepared resin and/or instead, a tocopherol. These micelles remain thermostable, so that there is no cloudiness even when the gel is boiled and the micelle structure does not get break-up even after large addition of water. The consistency is syrup-like or thinner. The gel is homogenised by stirring and is diluted to a suitable viscosity by the addition of water or water-solvent mixtures. However, if one homogenises with high shearing forces, then the formation of gel becomes harmful. The emerging gel is then not transparent, which means that along with solubilising a dispersing also has taken place. If the stirring is done with normal knives, such as the Stefan stirring machine, which has a rotating axis protruding vertically from the container base with sharp knives arranged perpendicular to that, which keep on cutting the mass to be stirred, or with a Diosna stirring machine, then the result is a visually clean, nice and transparent gel with very few air bubbles. In such a matrix, a microbial contamination proceeds much slower as compared to in a liquid.

The basic principle of the method, broadly formulated, is that one mixes the active agents with two required auxiliary substances, namely a poloxamer on one hand, and a resin and/or a tocopherol on the other, and when an extra low melting point is desired or necessary, optional solvents like glycerin, propylene glycol, polyethylene glycol 400, etc. are added in addition, in order to generate a molten mass at around 40° C. to 100° C. In this molten mass, all the components to be solubilised are brought in intimate contact with the surface and thereafter coated with water or combinations of water and optional solvents, as a result of which this coating has a temperature of 1° C. to 100° C.

By solubilising and stabilising the desired active agent coenzyme Q10 that stimulates the cell mitochondria, a dark-red transparent gel arises when covered with warm water. When the active agent Propolis is used, the transparent gel becomes dark yellow. In each case, however, a homogeneous and transparent gel arises through the water covering. As soon as this gel arises, the excess water can be poured away and the gel can be taken out of the container. It proves to be very robust and can be kneaded, pressed, drawn or rotated without changing its consistency. Depending upon the type of the active agent solubilised with poloxamer and resin or tocopherol through this method, different colours arise in the gel. The viscosity of the gel can be varied by using further additives and by dosing the water quantity used. The more water is added, the more fluid the gel becomes. Vice versa, the less water is added, the more viscous the gel becomes, till its consistency becomes similar to that of aspic. This variability of the consistency opens up new application options, such as the use of water-like concentrate in drinks, or the use of viscous gel in skin creams for an easy to spread consistency for care products or for lubricants in grease.

With this method, the bioavailability of an active agent, such as the coenzyme Q10 can be increased to about 85% in case of oral administration, because now the active agents are encapsulated on a molecular basis and remain stable even under the cmc of poloxamer through covering by means of poloxamer and resin or tocopherol. If one takes into account that in the year 2004 about 100 tons of the coenzyme Q10 were used worldwide, and the price/kg is CHF 2,000, then the economic impact of a substantial increase of the bioavailability can be measured.

An important point in relation to the disclosed method is that poloxamer, resin and tocopherol are mentioned in the standard reference works for the pharmacists and the pharmaceutical industries, namely in the international Pharmacopoeias. Not only the known active agents and auxiliary substances are described in these Pharmacopoeias in detail, but instead it can also be seen from these reference works, what properties the substances should have if one is permitted to use them. Their purity, their contents, residues, etc. are specified. Moreover, it is also described, how one handles these auxiliary and active agents, etc. For the US there is the US Pharmacopoeia of the FDA, in the European Union the EU Pharmacopoeia is applicable, Great Britain has its own British Pharmacopoeia, and then there is also a Japanese Pharmacopoeia. This is in the vanguard, because it is especially strict. Even Russia and China have their own Pharmacopoeias. When an auxiliary substance is added in the Pharmacopoeia, then it can be used anywhere within the scope of the conditions described therein.

In different Pharmacopoeias, poloxamer, various resins and tocopherol have a separate monograph, i.e. a complete substance description. The poloxamers are completely inert. Resins are hardly used regularly and are not highly effective while tocopherols (Vitamin E) are used often and are mildly effective. In no country one comes across any resistance with these substances, and they are already being used in many cosmetics, pharmaceutical and animal nutrition supplementary products.

Few active agents are mentioned below, for whose solubilisation and stabilisation the method is suitable. Vitamin C is a very useful active agent and is water-soluble as such. Vitamin C, however, is not very stable against light, air and in neutral pH range. When Vitamin C is dissolved in water, then in 2 to 3 days it becomes light yellow, then yellow and finally brown-red, which is a clear sign that it is undergoing structural changes and is thus also losing its effect. For this reason, one uses Vitamin C only sparingly or not at all, although its effect is recognised and would be desired, in many products such as in cosmetics and in food supplements. Vitamin C can be stabilised by means of the method disclosed here.

Another important active agent is insulin. Insulin is water-soluble by itself, but very troublesome with respect to its stability. Most of the applications requiring injection quickly lead to a deactivation of insulin. If one administers it orally and sends it through the gastrointestinal tract, it comes across hydrochloric acid and pepsin in the stomach, and then small quantity of intestine juice with cholesterol and bile acid. The effect of insulin gets reduced by these digestive juices. With the help of the dispersion and stabilisation method as described above, the bioavailability of insulin can be enhanced considerably, so that an oral administration is viable.

There is another series of active agents, which are normally sprayed in the nose by means of nasal sprays. Many such sprays contain auxiliary substances, which—especially when the spray is used over long periods of time—can cause allergies in the nasal mucosa, in the respiratory tract or even in the lungs. If one solubilises and stabilises these active agents with poloxamer and tocopherol as described above, then the allergic patients no longer react to the solubilised allergen. Poloxamer and tocopherol themselves do not cause any allergies, neither in use as a nasal spray nor in a drinking solution, and they isolate the allergens extremely effective.

It always turns out to be true that from the poloxamer and resin or tocopherol a molten mass is generated, which is then covered with water at the same temperature for specific applications. A special poloxamer, namely Lutrol F68, generates in the process a lower viscosity and can thus be used for solubilising and stabilising the active agents to be applied parenterally subsequently, whether via infusions or injections. Thus, in case of a commercial production, the risk of a fat embolism through the lipophilic active agent is less, because it does not precipitate in the blood.

Contact lenses, whose regular cleaning is very important, can be cleaned thanks to the use of a cleaning solution on the basis of this solubilisation method, without subsequently causing a burning sensation in the eyes. Such contact lenses are very delicate to clean. Now they can be cleaned properly and thoroughly with the solutions made according to the technology presented here, even without having to be taken out of the eye.

If poloxamer, resin or tocopherol are used according to the method, then lipophilic and resin-like active agents can be dissolved in hydrophilic milieu as well as also hydrophilic substances in lipophilic milieu. Solid particles can also be solubilised and dispersed in aqueous milieu. An application of this, for instance, is to isolate pollen in aqueous milieu and to transport it away. A nasal spray can be produced, which disperses the pollen penetrated in the nose, which irritates the mucous membrane there, so that a hay fever can be prevented. Used in a shampoo it can also fight dandruff by dispersing it in a similar fashion in aqueous milieu and then releasing it easily and without any mechanical effort from the skin and especially from the scalp. This makes cosmetic and dermatological applications possible, whether for humans or for animals.

Furthermore, drinks and syrups can also be produced for the dietary supplement of humans and animals, as well as pure drinks for humans and animals, which can also be enriched with oxygen and from which the "active agents" are reabsorbed as well. As already described, the method is extremely suitable for providing drugs for humans and animals to be applied locally, as well as drugs to be applied parenterally and solutions for humans and animals, which are enriched with oxygen. 5° C. to 10° C. cold deep spring water contains 12 to 18 mg oxygen per liter, and when the water is heated, this oxygen content quickly decreases. Micelles produced according to the method increase the inner surface, at which one can deposit the oxygen. A 1%, aqueous, unloaded micelle solution then keeps over 100 mg medical oxygen per liter water at 18° C. stable in a 10-liter bucket without lid, filled up to ⅔, for over 5 days! A large number of new applications of the products prepared according to the method also result in technical applications. Articles can be freed of fat residues. On the other hand, lubricants and fatty care products can also be produced by solubilising the fats.

The present method is especially suitable for the following substances and applications: Basically for solubilising lipophilic and hydrophilic substances for food supplements, for cosmetics and dermatological products, such as coenzyme Q10, vitamin C, vitamin E, beta-carotene, vitamin A, vitamin D3, lutein, lycopene, folic acid, vitamin B12, Ω-3 and Ω-6 fatty acids, for resin-like substances against infections, for the preservation of substances, for producing substances for wound dressing, for example, on the basis of propolis, selenium dioxide, tars and mineral oils. Furthermore, the method enables to make peptide orally bio-available, such as to solubilise insulin (anti-diabetic), cyclosporine, etc., as well as plant extracts from holy thistle, passion flower and butterbur, etc. and their derivatives (such as Silymarin, Chrysin etc.). In general, the polyphenyl compounds can be solubilised without any problems according to the method, which always achieves an active agent concentration of 2-5% in the solubilisate.

The following quantitative compositions of the gels made of poloxamer resin (or tocopherol) molten masses are typical: Active agent/s 1% to 10%, total poloxamer content 10% to 20%, resin or tocopherol 1% to 20% and the remaining water up to 100% gel weight. Gels, which are produced according to the described method via a molten mass, are characterised by their transparency, which remains even when diluted to a large extent with water or water-solvent mixtures. Only through a production via molten masses with poloxamer/s and resin or tocopherol, and active agent/s and optional solvents, such high concentrations of the active agent can be solubilised to completely transparent gels. Through a suitable addition of solvents, the viscosity of the gel can be reduced and/or the molten mass can be produced at lower temperatures. In this production method, the covered molten masses of auxiliary substances permit a large number of solubilisations: Thus the active agent content of solubilised, hydrophilic ascorbic acid can be around 10% in oil, similarly, lipophilic coenzyme Q10 can be solubilised in water with 2%-6% in the same way as resin-like propolis.

In case of insulin as the active agent, not only a homogeneous, stable and concentrated dispersion is achieved, but also the oral bioavailability of this active agent is increased substantially. Since the poloxamers are mentioned in all the medical books and in Switzerland are even mentioned as additives in the list of fodder, they can be used for the oral administration and even parenterally for grade 188 of poloxamer. Given below are some detailed examples of how the method can be implemented.

Example 1

Stabilisation of Vitamin C and ACC in a Shampoo Containing ACC, Vitamin C and Vitamin E

| A | water | 74.11% |
|---|---|---|
| B | sodium laureth sulphate | 11.67% |

-continued

| | | |
|---|---|---|
| C | cocamidopropyl betain | 2.00% |
| D | cocamide DEA | 1.70% |
| E | disodium laureth sulfosuccinate | 1.32% |
| F | perfume | 1.00% |
| G | poloxamer 407 | 1.40% |
| H | poloxamer 188 | 0.60% |
| I | ascorbic acid | 1.00% |
| J | acetyl cysteine | 1.00% |
| K\ | alfa tocopherole | 0.50% |
| L | sodium lauryl sulphate | 0.80% |
| M | phenoxyethanol | 0.50% |
| N | imidazolidinyl urea | 0.20% |
| O | PEG-120 methyl glucose dioleate | 0.10% |
| P | tetrasodium EDTA | 0.10%. |

The production process is as follows:
Heat G, H and K to 60° C. till they melt,
Mix I and J and disperse in the molten mass under stirring,
Cover with a quarter of A (60° C. warm) and wait for the gel to form→Gel,
Take three-fourths of A and add successively B, C, D, E, F, L, M, N, O, P under stirring after weighing→transparent solution,
Add the gel and then add the solution under stirring.

Example 2

Solubilisation Example for Coenzyme Q10 in a Gel Containing Vitamin C and Vitamin E

| | |
|---|---|
| Water | 71.43% |
| Poloxamer 188 | 8.93% |
| Poloxamers 407 | 8.93% |
| Alpha Tocopherol | 5.00% |
| Coenzyme Q10 | 2.14% |
| Ascorbic acid | 3.57% |

Example 3

Solubilisation Example for a Gel Containing Propolis

| | |
|---|---|
| Water | 70% |
| Poloxamer 188 | 18% |
| Propolis | 12% |

For sake of preciseness and clarity, some definitions and explanations are given below:
Tensides are compounds whose molecules contain a hydrophilic (affinity to water) and a lipophilic part (affinity to fats).
Due to this fact, the tensides enrich themselves in the interface at the water phase, i.e. they are surface-active. They do this regardless of the fact whether the water phase comes in contact with a gaseous, a liquid or a solid phase.
Moreover, upon exceeding a specific tenside concentration, large molecular structure of tensides form in the solution, which are in equilibrium with the individual molecules. The molecular structures can have different shapes and sizes, but have a spherical shape in the simplest case.

Upon exceeding a specific concentration, characteristic for the respective tenside, the tenside molecules aggregate together in such a way that a shape is formed, whose inside comprises of lipophilic groups, and at whose surface the hydrophilic groups are present, which make contact with water and thus also determine the solubility of the structure in water.

The aggregates are known as micelles and these molecular groups can dissolve again, when one dilutes the system with water for so long that the concentration of the tenside falls below the characteristic value, which one calls the "critical micelle formation concentration" or "cmc" in short.

The "cmc" of a tenside is higher, the less lipophilic the non-polar part of the tenside molecule is.

The inner part of the micelle is present in the liquid state.

In most of the cases, only mono-tensides are present in solutions below the "cmc". Above the "cmc" the number of the aggregates remains almost always constant. The entire additional tenside material is above the "cmc" only in the form of micelles, so that the micelle formation can be viewed as the formation of a new phase, in which, however, the aggregation number does not grow infinitely.

The concentration of the dissolved mono-tensides, therefore, cannot be increased above the "cmc".

The temperature, at which the dissolution of the tensides takes place due to the incipient micelle formation, is known as the Krafft point of the tenside. Since this Krafft point represents a quite sharply defined temperature, it appears as if the undissolved tenside would melt upon reaching the Krafft point. The Krafft point is therefore often compared with the melting point.

Non-ionic tensides, which form a clear solution in water, show a special behaviour in contrast to other tensides. In case of temperature increase, the solution becomes cloudy upon exceeding a specific, relatively and clearly defined temperature, which is characteristic for the respective tenside, and the solution gets dissociated in two liquid phases. This temperature is known as turbidity point.

The reason for the occurrence of this phenomenon depends on the hydration of the hydrophilic non-ionic groups. In case of increasing temperature, a partial dehydration takes place, which leads to the formation of a new phase. For this reason, the turbidity point is almost independent of the total concentration of the tenside. However, this turbidity can be reversed upon cooling. The turbidity point can be influenced through additives: Additives can be stored in the micelles interstitially and modify their properties or they can modify the properties of water, i.e. the surroundings of the micelles. The latter mechanism especially applies to the addition of the electrolytes, which generally displace the turbidity point towards lower temperatures with increasing concentration.

The spherical shape of the micelles arises because the hydrophilic header groups want to be away from one another as far as possible due to electrostatic repulsion and at the same time also want to have contact with the surrounding water molecules. The lipophilic molecule parts inside the micelles are not in contact with water; the size of the micelles is based on the space required by the lipophilic group.

The following data is applicable for Pluronic:

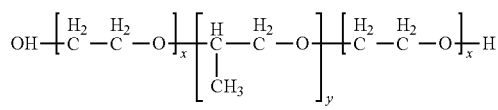

Pluronic F127: EO100-PO65-EO100
Pluronic F68: EO76-PO29-EO76
Pluronic P85: EO26-PO40-EO26

| Polymer | Molecular weight | HLB value | CMC (g/lt) | Micelle diameter |
|---|---|---|---|---|
| Pluronic P85 | 4600 | 26 | 1.058 | 1.5 nm |
| Pluronic F68 | 8400 | 29 | 1.344 | 1.3 nm |
| Pluronic F127 | 12600 | 22 | 0.869 | 3.3 nm |

(Z. Sezgin et al./European Journal of Bio-pharmaceutics 64 [2006] 261-268)

Some more explanations are given below:

In case of spherical micelles, the radius can grow only till the length of the lipophilic molecular part. The number of the mono-tensides per spherical micelle (=aggregation number) is thus restricted upward and is given by the volume requirement of a lipophilic molecular part in proportion to the total volume of the micelle.

In case the concentration of the tenside is increased, the size of the micelles thus remains constant and only their number increases.

An important property of the micelles is their ability to solubilise other molecules. Since micelles practically represent small hydrocarbon droplets, they are in a position to dissolve the lipophilic substances. These water-insoluble substances are integrated in the inside of the micelles and are no longer in contact with water. However, since the surface of the micelles is hydrophilic, the active agent floats if dissolved in water. This process is known as solubilisation. Micelles are stable systems in the thermodynamic sense. The concentration of the particles solubilised through tensides lies mostly below 5%. The interface causes a light scattering (Tyndall effect), the system often appears to be turbid.

Solubilisation (=deposition of lipophilic substances in the inside of the micelles) lets the micelles grow, so that the additional tensides are deposited on the micelle surface. The diameter of the micelles thereby grows in case of Pluronic F68 upwards from 1.3 nm (uncharged) and in case of Pluronic F127 upwards from 3.3 nm (uncharged). The micelle diameter normally lies below 140 nm. However, these sources of micelles can lead to a particle size of the solubilisate of up to 500 nm, where the solubilisate appears almost transparent with a bluish shimmer. In case of particle sizes below 140 nm, the solubilisate appears only transparent.

The HLB value (Hydrophile Lipophile Balance) quantifies the hydrophilic and the lipophilic portion in the tenside molecule. This value is an expression of the properties of the tenside molecule. The HLB value of Pluronic F68 is 29, of Pluronic F127 is 22. Both the tensides are strong hydrotropes.

For a clear solubilisation of perfume oils, essential oils and oil-soluble vitamins, tensides having an HLB value of 14-17 are used. These substances are also known as hydrotropes or solubilisers. Due to their high HLB value the solubilisers generally have a tendency of foaming, which causes technical problems. Both Pluronics (F68 and F127), however, are foam killers.

Mainly the perfume oils, which contain resins, resinoids, terpene, ester or ketones, are poorly soluble in water and must be solubilised in aqueous systems.

Resins, resinoids and their esters, in turn, are very good solvents for essential oils, oil-soluble vitamins, polyphenyl compounds and other lipophilic active agents. At the same time, resins, resinoids and their esters can also be solubilised very well by the tensides Pluronic F127, Pluronic F68 and Pluronic P85.

Abamectin is a mixture of >=80% Abamectin $B_{1a}$ (M: 873.1; $C_{48}H_{72}O_{14}$) and <=20% Abamectin $B_{1b}$ (M: 859.1; $C_{47}H_{70}O_{14}$). These are colourless to slightly yellow crystals with a melting point of 161.8-169.4° C. (under decomposition) and a density of 1.18 at 25° C. Abamectin is stable against hydrolysis in aqueous solutions at pH 5, 7 and 9 (at 25° C.). With about 2 g of Abamectin finely distributed in 1000 liter of water, an area of one hectare (two football fields) can be sprayed in about an hour. With the help of a sample formulation for the active agent Abamectin, which is a very potent acaricide (against mites), it can be shown that apart from a good solubility of Abamectin in a resin mixture, and apart from a good solubilisation of the resin-Abamectin-solution by means of Pluronic, there is also a unique, never-before observed stability of the solubilisate made according to this method even below the "cmc" characteristic for Pluronic of 1.344 g/lt (F68), or 0.869 g/lt (F127) and above the solubility limit of 7-10 mcg/lt Abamectin in water (25° C.).

The water-free formulation with a possibly high Abamectin concentration, which can be mixed with water in any ratio without any problem and always produces transparent results, is as follows:

| Abamectin 'solid solution' 4.6%-ig | | |
|---|---|---|
| | in g | in % |
| Pluronic F68 | 32.5 | 32.5 |
| Pluronic F127 | 32.5 | 32.5 |
| Alpha-Tocopherol | 9.9 | 9.9 |
| Resin | 19.7 | 19.7 |
| Abamectin 85%-ig | 5.4 | 5.4 |
| TOTAL | 100.00 | 100.0 |

The formulation in case of "cmc" of Pluronic F127 (=0.869 g/lt):

| Abamectin 'solubilisat 0.01%-ig | | |
|---|---|---|
| | in g | in % |
| Lutrol F68 | 0.869 | 0.087 |
| Lutrol F127 | 0.869 | 0.087 |
| Alpha-Tocopherol | 0.265 | 0.026 |
| Resin | 0.527 | 0.053 |
| Abamectin 85%-ig | 0.144 | 0.014 |
| Water | 997.326 | 99.733 |
| TOTAL | 1000.000 | 100.0 |

With 122,000 mcg/lt the Abamectin concentration lie in water at the "cmc" of Pluronic F127 which is much above the solubility of 7-10 mcg Abamectin per liter of water. Still, the solubilisate remains stable and transparent upon a further dilution with water. This result cannot be generated with any other production process known so far with the same formulation. The micelles thus produced also remain stable under the cmc, as when the resin used is not only the solvent for Abamectin and can be dissolved properly with Pluronic, but also enters in a special bonding with Pluronic and in this way keeps the micelles stable even at extreme dilution with water. A typical usage concentration for Abamectin is 2,000 mcg/lt, i.e. a concentration, which lies above the solubility limit for Abamectin in water and thus should be dissolved in micelles. A formulation of the resin mixture (resins):

| Resin | | |
|---|---|---|
| | in g | in % |
| Benzyl benzoate | 467 | 46.7 |
| Cinnamic acid benzyl ester | 233 | 23.3 |
| Alpha-Tocopherol | 100 | 10.0 |
| Cinnamon alcohol | 100 | 10.0 |
| Benzoic acid | 100 | 10.0 |
| TOTAL | 1000 | 100.0 |

The following components are used:
Resins:
Benzyl benzoate (M: 212.2; $C_{14}H_{12}O_2$) is a colourless liquid or colourless crystals; practically insoluble in water (prevents crystallisation).
Cinnamic benzyl ester (M: 238.29; $C_{16}H_{14}O_2$; density: 1.106) are white, aromatic crystals; practically insoluble in water.
or optionally benzyl coniferyl ester.
Antioxidants: Alpha tocopherol.
Solvents: Cinnamyl alcohol, benzyl alcohol, ethyl diglycol, dipropylene glycol, PEG 400, benzoic acid.

If one sets the Abamectin solubilisate with water to an active agent concentration between 2% and 0.5%, then one gets gel-shaped transparent preparations, which make a sound, when one strikes a glass full of this gel on a hard surface. This "ringing" is also noticeable as a vibration. Such ringing gels are extremely stable in heat and in cold. The effect of this stable structure is also that active agents sensitive to hydrolysis remain stable as a result of the deposition in the system at high temperatures.

Examples

| Abamectin 'solubilisate 1.6%-ig | | |
|---|---|---|
| | in g | in % |
| Pluronic F68 | 130.17 | 13.0 |
| Pluronic F127 | 130.17 | 13.0 |
| Alpha-Tocopherol | 34.2 | 3.4 |
| Resin | 68.48 | 6.8 |
| Abamectin 85%-ig | 18.6 | 1.9 |
| Aqua | 618.38 | 61.8 |
| TOTAL | 1000.00 | 100.0 |

| Abamectin 'solubilisate 0.88%-ig | | |
|---|---|---|
| | in g | in % |
| Pluronic F68 | 83.35 | 8.3 |
| Pluronic F127 | 83.35 | 8.3 |
| Alpha-Tocopherol | 21.94 | 2.2 |
| Resin | 43.82 | 4.4 |
| Abamectin 85%-ig | 10.24 | 1.02 |
| Aqua | 757.3 | 75.7 |
| TOTAL | 1000.00 | 100.0 |

When dry solids are stored unprotected in air charged with water vapour, a sorption takes place depending upon the moisture content of the air and the hygroscopic properties of the solids, i.e. a vapour absorption takes place. In such a process, either only a few molecular layers are bonded on the solid surface through adsorption or penetrates in the mass of the solid, which is known as absorption. Adsorption, on the other hand, occurs when moist solids give out water vapour in dry atmosphere.

Solid or semi-solid concentrates of active agent, which are extracted according to the described method by producing a molten mass or gel of the active agent, where these molten masses and gels then show charged water-vapour and thus hydrophilic and/or water-soluble solids with a large surface, or a surface enlarged due to spraying and/or freeze drying, offer excellent properties for the re-absorption of active agents in the human or the animal body. These properties are independent of, whether the concentrates of the active agents are finally subject to a desorption or not. With the method described above, therefore, solid concentrates of active agents can be produced for the oral use, which can be filled in gelatine capsules, packed in sachets as dosed powder or compressed in the form of tablets and effervescent tablets. After their decomposition and dissolution in water or in the gastric juice in humans or animals, the active agents are present in solubilised and/or dispersed form, which can be absorbed quickly and completely. Similarly, semi-solid concentrates of active agents can also be produced with good resorption properties, which can subsequently be filled in soft gelatine capsules.

The following are especially suitable as hydrophilic or water-soluble solids with large surfaces or surfaces enlarged due to spray or freeze drying (specific surface>0.01 $m^2/g$ BET method):
Exudates, such as gum arabic, tragacanth, karaya gum, ghatti gum,
Seed flours, such as guar gum, carob bean flour, tara stone flour, tamarind gum,
Detergent builders, such as larch gum, pectin, agar, alginate, carrageen, furcellaran,
Bio-synthetic hydrocolloids, such as xanthan,
Modified hydrocolloids, such as propylene glycol alginate, amidated pectin,
Cellulose derivatives, such as methyl cellulose, methyl ethyl cellulose, methyl hydroxyl ethyl cellulose, methyl hydroxyl propyl cellulose, hydroxyl propyl cellulose, sodium carboxy-methyl cellulose,
Silicon oxides, such as Aerosil,
Proteins, such as gelatine, skimmed milk powder,
Sugars, such as lactose, mannitol, xylite, sorbitol, dextran.

As another aspect of the invention, now its use for the application as active agent for plants will be discussed. At first, method for solubilising and stabilising an active agent for plants will be presented in more detail. It has been proved to be especially important that the active and the auxiliary substances, i.e. here abamectin and poloxamer amalgamate with resin and tocopherol on a molecular basis and thus form a quasi active-auxiliary-complex. A simple mixing of all components with subsequent stirring leads to a content of maximum of some tenth percentage of the added active agent for plants. The melting point of pure poloxamers lies at around 57° C. to 58° C. This type of dissolution, in which one merges the poloxamer, the resin or a tocopherol in a molten mass on molecular or quasi-molecular basis with the active agent for the plant to be solubilised, proves itself as the key for improving the processing of the active agent.

Broadly formulated, the principle says that one mixes two required auxiliary substances, namely poloxamer and resin or tocopherol with an optional solvent as well as with the active agent for the plants and generates a molten mass from these at around 40° C. to 100° C., as a result of which the protagonists are brought in an inner, quasi-molecular contact with one another. A poloxamer, namely Poloxamer 188 and/or Poloxamer 407 and/or one of their substitutes and/or derivatives are melted and the active agent for the plants to be treated is dispersed inside this molten mass. The melting temperature can be lowered by adding solvents. These solvents could be, for instance, water, glycerine, propylene glycol, polyethylene glycol 400, ethanol, Macrogol 400 or isopropanol. After adding the active agent for plants to be treated in this molten mass, it is cooled, till it becomes brittle. This can be accelerated by adding dry ice. Thereafter, this hardened molten mass is milled in a mill, chopped in the mill by means of knives and then rolled with water in an emulsion mill, till the melt crystals have been reduced to such an extent that their diameter is 5 micrometer or less. The emulsion mill advantageously has a cooled shearing head, so that the melt crystals do not become excessively hot during milling and retain their brittle consistency. Despite the brittleness of the material, these processes run dust-free. In this emulsion mill, the reduced melt suspension of the gear system can run several times in a circulation, whereby it becomes smaller and smaller, till it has achieved an adequate fineness. These smallest crystals remain thermostable and the tenside surface is not "washed away" upon a further addition of water. The melt crystals are then dissolved in water or dispersed and put in the ground area near the plants for absorption through their roots, or the solution is sprayed directly on to the part of the plant above the ground. Another advantage results from the stability of the micelles. Active agents, which are sprayed on the plants according to the method as a solubilisate and are dried on their surface due to evaporation, can be washed away easily from the surface of the plant after harvesting. In this way, an unpeeled, sprayed apple does not taste bitter after being washed quickly with water.

With this method, the bio-availability of an active agent for plants can be enhanced considerably, because now the active agent is incorporated on a molecular basis and coating of poloxamer-resin-tocopherol remains stable (quasi-complex) even when diluted highly with water. If different molten masses of active agent-poloxamer-resin-tocopherol are combined in water, then each module retains its physical properties. There is no influencing amongst one another, as well as other surface-active tensides also do not affect these complexes in water. Basically, poloxamer-resin-tocopherol used in this method are used for solubilising and dispersing each of the lipophilic active agent for plants.

As already described above, poloxamers have a monograph in the different Pharmacopoeias, i.e. a complete description of the active agent. The poloxamers are completely inert. They may be used in the agricultural, the cosmetics and the animal nutrition sectors. Individual poloxamers are used in parenteral drugs. Poloxamers are, therefore, harmless.

If poloxamer, resin or tocopherol are used according to the method, then lipophilic and resin-like active agents for plants can be dissolved in hydrophilic milieu as also hydrophilic substances in lipophilic milieu. Solid particles can also be solubilised and dispersed in aqueous milieu. An application of this is, for instance, solubilising the pollen in aqueous milieu.

The following quantitative compositions are typical for poloxamer molten masses: 0.1% to 8% active agent for plants, approx. 10-20% poloxamer and 1-15% of a natural or an artificially prepared resin (or a tocopherol in its place). Such compositions are then solubilised or suspended in water.

Solid or semi-solid concentrates of active agents for plants, which are extracted according to the method described above by preparing a molten mass of the active agent, such that this molten mass has a large surface for stirring the auxiliary or the active agent, as is normally achieved through spray and/or freeze drying, offer excellent properties for the absorption of the active agents in the plants. These properties are independent of, whether the concentrates of the active agents are finally subject to a desorption or not. With the method described above, therefore, solid concentrates of active agents for plants can be prepared. The melt crystals are then absorbed by the plant together with the water, in which they are solubilised, through their root network.

Explicitly, the invention also includes the application of the molten mass, as described above, on water-soluble macromolecules, which is further supposed to increase the contact surface of the poloxamer-resin-tocopherol complex of the active agent. The following are suitable as hydrophilic or water-soluble solids with large surfaces or with surfaces increased through spray and/or freeze drying (specific surface>0.01 $m^2/g$ BET method):

Exudates, such as gum arabic, tragacanth, karaya gum, ghatti gum,

Seed flours, such as guar gum, carob bean flour, tara stone flour, tamarind gum, Detergent builders, such as larch gum, pectin, agar, alginate, carrageen, furcellaran, Bio-synthetic hydrocolloids, such as xanthan, Modified hydrocolloids, such as propylene glycol alginate, amidated pectin, Cellulose derivatives, such as methyl cellulose, methyl ethyl cellulose, methyl hydroxyl ethyl cellulose, methyl hydroxyl propyl cellulose, hydroxyl propyl cellulose, sodium carboxy-methyl cellulose, Silicon oxides, such as Aerosil, Proteins, such as gelatine, skimmed milk powder, Sugars, such as lactose, mannitol, xylite, sorbitol, dextran.

What is claimed is:

1. A stabilized product comprising a transparent gel that comprises at least one polyoxyethylene-polyoxypropylene block copolymer (poloxamer), a natural or an artificially prepared resin and/or a tocopherol, and an active agent, said active agent being one or more substance selected from the group consisting of insulin, cyclosporine, polyphenyl compounds, propolis, selenium dioxide, tar, mineral oil, plant extracts from holy thistle, plant extracts from passion flower, plant extracts from butterbur, silymarin, and chrysin; said stabilized product being formed by (a) melting said at least one poloxamer and said resin and/or said tocopherol together at an elevated temperature to form a molten liquid mass, (b) solubilizing or dispersing the active agent within said molten liquid mass without addition of water, and (c) then covering the molten liquid mass containing solubilized or dispersed active agent with water having a temperature at about said elevated temperature, thereby forming said transparent gel which contains micelles that retain and/or bind the active agent, wherein said micelles have a diameter less than 80 nanometers and are stable in water when diluted below critical micelle concentration of the poloxamer.

2. The stabilized product according to claim 1, wherein said micelles are stable in water when diluted to 1000 times below the critical micelle concentration of the poloxamer.

3. The stabilized product according to claim 1, wherein said molten mass comprises about 10 to 20% of said poloxamer, 1 to 20% of said resin and/or a tocopherol, and about 1 to 10% of said active agent.

4. The stabilized product according to claim 1, wherein said poloxamer includes poloxamer 188, poloxamer 407, or combinations thereof.

5. The stabilized product according to claim 1, wherein said molten liquid mass further comprises a solvent selected from the group consisting of glycerine, propylene glycol, ethanol and isopropanol.

6. The stabilized product according to claim 1, wherein said molten liquid mass of step (b) is water-free.

7. The stabilized product according to claim 1, wherein said elevated temperature is 40-100° C.

8. The stabilized product according to claim 1, wherein said transparent gel contains a concentrate of the active agent.

* * * * *